United States Patent
Maitro-Vogel et al.

(10) Patent No.: US 9,428,432 B2
(45) Date of Patent: Aug. 30, 2016

(54) DERIVATIVES OF TRIS(2-HYDROXYPHENYL)METHANES, PREPARATION THEREOF AND USE THEREOF FOR MINERAL OIL PRODUCTION

(71) Applicant: BASF Wintershall Holding GmbH, Kassel (DE)

(72) Inventors: Sophie Maitro-Vogel, Mannheim (DE); Roman Benedikt Raether, Speyer (DE); Markus Hansch, Speyer (DE)

(73) Assignee: BASF Wintershall Holding GmbH, Kassel (DE)

( * ) Notice: Subject to any disclaimer, the term of this patent is extended or adjusted under 35 U.S.C. 154(b) by 521 days.

(21) Appl. No.: 13/683,618

(22) Filed: Nov. 21, 2012

(65) Prior Publication Data

US 2013/0228332 A1    Sep. 5, 2013

Related U.S. Application Data

(60) Provisional application No. 61/563,564, filed on Nov. 24, 2011.

(51) Int. Cl.

| | |
|---|---|
| *B01F 17/00* | (2006.01) |
| *C07C 41/03* | (2006.01) |
| *C07C 43/23* | (2006.01) |
| *C07C 51/41* | (2006.01) |
| *C07C 59/68* | (2006.01) |
| *C07C 59/72* | (2006.01) |
| *C07C 67/26* | (2006.01) |
| *C07C 69/734* | (2006.01) |
| *C09K 8/584* | (2006.01) |
| *C11D 1/72* | (2006.01) |
| *E21B 43/16* | (2006.01) |

(52) U.S. Cl.
CPC ........... *C07C 43/23* (2013.01); *B01F 17/0021* (2013.01); *B01F 17/0028* (2013.01); *C07C 41/03* (2013.01); *C07C 51/412* (2013.01); *C07C 59/68* (2013.01); *C07C 59/72* (2013.01); *C07C 67/26* (2013.01); *C07C 69/734* (2013.01); *C09K 8/584* (2013.01); *C11D 1/72* (2013.01); *E21B 43/16* (2013.01)

(58) Field of Classification Search
CPC ........... B01F 17/0021; B01F 17/0028; C07C 41/03; C07C 43/23; C07C 51/412; C07C 59/68; C07C 59/72; C07C 67/26; C07C 69/734; C09K 8/584; C11D 1/72; E21B 43/16

See application file for complete search history.

(56) References Cited

U.S. PATENT DOCUMENTS

| | | |
|---|---|---|
| 4,978,780 A | 12/1990 | Fikentscher et al. |
| 5,668,227 A | 9/1997 | Wolleb et al. |
| 5,741,947 A | 4/1998 | Wolf et al. |
| 7,335,235 B2 | 2/2008 | Ruland et al. |
| 7,461,694 B2 | 12/2008 | Dahanayake et al. |
| 2005/0155762 A1 | 7/2005 | Chen et al. |
| 2005/0170991 A1 | 8/2005 | Ruland et al. |
| 2009/0155714 A1 | 6/2009 | Lee et al. |
| 2011/0083846 A1 | 4/2011 | Bittner et al. |
| 2011/0083847 A1 | 4/2011 | Bittner et al. |
| 2011/0083848 A1 | 4/2011 | Bittner et al. |
| 2011/0118365 A1 | 5/2011 | Steiner et al. |
| 2011/0220353 A1 | 9/2011 | Bittner et al. |
| 2011/0220364 A1 | 9/2011 | Bittner et al. |
| 2011/0220365 A1 | 9/2011 | Bittner et al. |
| 2011/0220366 A1 | 9/2011 | Bittner et al. |
| 2011/0259583 A1 | 10/2011 | Bittner et al. |
| 2011/0263467 A1 | 10/2011 | Bittner et al. |
| 2011/0281779 A1 | 11/2011 | Weerasooriya et al. |
| 2011/0288322 A1 | 11/2011 | Garcia et al. |

FOREIGN PATENT DOCUMENTS

| | | |
|---|---|---|
| DE | 4325237 A1 | 2/1995 |
| DE | 10243361 A1 | 4/2004 |
| EP | 311 961 A2 | 4/1989 |
| EP | 0597806 A1 | 5/1994 |
| EP | 10163371.7 | 5/2010 |
| EP | 11185626.6 | 10/2011 |
| WO | WO-2008100436 A1 | 8/2008 |

OTHER PUBLICATIONS

U.S. Appl. No. 61/312,299.
U.S. Appl. No. 61/550,465.
U.S. Appl. No. 61/325,051.
U.S. Appl. No. 61/315,051.
Casiraghi, et al. "Regiospecific Reactions of Phenol Salts: Reaction-Pathways of Alkylphenoxy-Magnesiumhalides with Triethylorthoformate" Tetrahedron Letters No. 9 (1973) pp. 679-682.
Dinger, et al. "Alkali Saltes of C3-Symmetric, Linked Aryloxides: Selective Binding of Substrates with Metal Aggregates" lnorg. Chem. (2000) vol. 39, pp. 1238-1254.

(Continued)

*Primary Examiner* — Paul A Zucker
*Assistant Examiner* — Mark Luderer
(74) *Attorney, Agent, or Firm* — Drinker Biddle & Reath LLP

(57) ABSTRACT

Novel derivatives of tris(2-hydroxyphenyl)methanes which have, as functional groups, polyalkoxy groups unmodified or modified with terminal hydrophilic groups, preparation of such compounds and use thereof, especially for mineral oil production.

24 Claims, No Drawings

(56) References Cited

OTHER PUBLICATIONS

Dinger, et al. "Extended Structures Built on a Triphenoxymethane Platform—C3-Symmetric, Conformational Mimics of Calix[n]arenes" Eur. J. Org Chem. (2000) pp. 2467-2478.

Dinger, et al. "Selective Binding of Substrates Using Sodium Saltes of Linked C3 Symmetric Aryl Oxides" Chem. Commun. (1999) pp. 2525-2526.

Dinger, et al. "Synthesis, Characterization, and Reactivity of Multinuclear Zinc(II) Alkyl Derivatives of Linked Phenoxides" Inorg.Chem. (2001) vol. 40, pp. 1029-1036.

Hoffmann, et al. "The Influence of the Salt Concentration on the Aggregation Behaviour of Viscoelastic Detergents" Advances in Colloid and Interface Science (1982) vol. 17, pp. 275-298.

Matloka, et al. "C3-Symmetric Tripodal Thio/Diglycolamide-Based Ligands for Trivalent f-Element Separations" Separation Science and Technology (2006) vol. 41, pp. 2129-2146.

Matloka, et al. "Highly Efficient Binding of Trivalent f-elements From Acidic Media with a C3-Symmetric Tripodal Ligand Containing Diglycolamide Arms" Dalton Trans., (2005) pp. 3719-3721.

Mitra, et al. "Synthesis and Reactivity of a C3-Symmetric Trinuclear Zinc(II) Hydroxide Catalyst Efficient at Phosphate Diester Transesterification" Dalton Trans. (2007) pp. 3924-3935.

Peters, et al., "Enhanced Selectivity for Actinides over Lanthanides with CMPO Ligands Secured to a C3-Symmetric Triphenoxymethane Platform" Inorganic Chemistry (2002) vol. 41, No. 7, pp. 1707-1716.

Rojas, et al. "Effect of Ionic Environment on the Rheology of Wormlike Micelle Solutions of Mixtures of Surfactants With Opposite Charge" Journal of Colloid and Interface Science (2010) vol. 342, pp. 103-109.

Versteeg, et al. "An Environmental Risk Assessment for DTDMAC in the Netherlands" (1992) Chemosphere, vol. 24, No. 5, pp. 641-662.

DERIVATIVES OF TRIS(2-HYDROXYPHENYL)METHANES, PREPARATION THEREOF AND USE THEREOF FOR MINERAL OIL PRODUCTION

CROSS-REFERENCE TO RELATED APPLICATIONS

This application claims benefit (under 35 USC 119(e)) of U.S. Provisional Application 61/563,564, filed Nov. 24, 2011, which is incorporated by reference.

The present invention relates to novel derivatives of tris(2-hydroxyphenyl)methanes which have, as functional groups, polyalkoxy groups unmodified or modified by terminal hydrophilic groups. It further relates to the preparation of such compounds and to the use thereof, especially for mineral oil production.

Tris(2-hydroxyphenyl)methanes and various derivatives thereof are known in principle.

G. Casiraghi, G. Casnati and M. Cornia (Tetrahedron Letters, No. 9, 679 to 682, 1973) describe the synthesis of mono- or dialkylated tris(2-hydroxyphenyl)methanes by reaction of appropriate phenols with triethyl orthoformates.

M. B. Dinger and M. J. Scott describe, in Chem. Commun., 1999, 2525-2526, Inorg. Chem. 2000, 39, 1238-1254 and Inorg. Chem. 2001, 40, 1029-1036, the synthesis of various tris(3,5-dialkyl-2-hydroxyphenyl)methanes, the alkyl radicals described being methyl, t-butyl and t-pentyl radicals. The trishydroxyl compounds are used as complexing agents for zinc and alkali metal ions.

M. B. Dinger and M. J. Scott, Eur J. Org. Chem. 2000, 2467-2478 also describe the further conversion of the OH group of tris(3,5-dialkyl-2-hydroxyphenyl)methanes. The OH functions can be derivatized by reaction with halocarboxylic esters and hydrolysis and/or further conversions. Dinger and Scott describe, for example, tris(3,5-di-t-butyl-2-carboxymethoxyphenyl)methane, tris(3,5-di-tert-butyl-2-[(dimethylamido)methoxy]phenyl)methane, tris{3,5-di-tert-butyl-2-[N-(methylglycyl)carbonylmethoxy]phenyl}methane and tris(3,5-di-tert-butyl-2-[(benzylaminocarbonyl)methoxy]phenyl)methane. The derivatives can each be used as complexing agents, for example for Zn(II) ions.

K. Matloka, A. Gelis, M. Regalbuto, G. Vandegift and M. J. Scott, Dalton Trans., 2005, 3719 to 3721 or Separation Science and Technology, 41, 2006, 2129 to 2146, and M. W. Peters, E. J. Werner and M. J. Scott, Inorg. Chem., 2002, 41, 1701 to 1716, disclose functionalized tris(3,5-dialkyl-2-hydroxyphenyl)methanes, specifically tripodal diglycolamides, and the use thereof for complexation and removal of lanthanides. Synthetic intermediates used are tris(3,5-dialkyl-2-hydroxyphenyl)methanes in which the OH group has been etherified with ω-amino- or cyanoalkyl groups.

R. Mitra, M. W. Peters and M. Scott, Dalton Trans., 2007, 3924 to 3935, describe particular tris(2-hydroxyphenyl) methane derivatives which have terminal 2-pyridylmethyl-piperazine groups. These molecules can bind zinc ions and are used as catalysts for phosphate diester synthesis. An intermediate disclosed in the multistage synthesis is tris[2-(2-hydroxyethoxy)-3-methyl-5-t-butylphenyl]methane.

EP 0 597 806 A1 discloses glycidyl ethers containing cyclohexyl groups for use as reactive diluents, flexibilizers or adhesion improvers. Synthesis intermediates described include various tris(2-hydroxyphenyl)methanes, also including those in which the OH function has been etherified with a (substituted) 2-hydroxyethyl group.

US 2009/0155714 A1 discloses compositions for production of photoresists. Components used therefor include various tris(2-hydroxyphenyl)methane derivatives in which the OH function has been esterified with different carboxylic acids in each case.

It is known that surfactants aggregate above the critical micelle formation concentration (cmc) to form micelles. The shape of these water-soluble aggregates depends on the structure of the surfactants and on external parameters such as temperature or electrolyte concentration. Typically, spherical or rod-shaped micelles can form above the micelle formation concentration.

Given particular structural features and/or external parameters, it is also possible for long thread-like or worm-like micelles or associates to form. A consequence of this is that, even at relatively low surfactant concentration, there is interlooping and overlapping of these long aggregates, which cause the viscosity of the surfactant solution to rise significantly. A particular minimum period of micelle stability is a prerequisite. This temporarily formed network of surfactant micelles, from a rheological point of view, reacts both in a viscous and elastic manner, which is why reference is generally made to viscoelastic surfactant solutions. Micelles release individual surfactants, absorb surfactants into the micelle association, decompose and reform. Surfactant micelles which form viscoelastic networks are stable for very long periods before they fall apart into individual fragments and reform, such that the micellar network can offer resistance to shearing of the surfactant solution and hence reacts both in a viscous and elastic manner. Further details regarding surfactants which form viscoelastic, worm-like micelles, for example hexadecyltrimethylammonium p-toluenesulfonate or cetylpyridinium salicylate, are described, for example in H. Hoffmann et al., Adv. Colloid Interface Sci. 1982, 17, 275-298, or M. R. Rojas et al., Journal of Colloid and Interface Science 342 (2010) 103-109.

On the basis of the properties described, viscoelastic surfactants are of very particular suitability as thickeners and can be used in various fields of industry.

US 2005/0155762 discloses betaines with alkyl chains of 14 to 24 carbon atoms, for example oleylamidopropylbetaine or erucylamidopropylbetaine, as thickening viscoelastic surfactants.

U.S. Pat. No. 7,461,694 B2 discloses zwitterionic surfactants with alkyl chains of 16 to 24 carbon atoms as viscoelastic surfactants.

WO 2008/100436 A1 discloses a viscoelastic surfactant mixture composed of cationic, anionic or zwitterionic surfactants and a polymer. The surfactants have alkyl chain lengths of 12 to 25 carbon atoms.

In the disclosures cited, surfactants with long alkyl chains are used in each case for formation of viscoelastic surfactant solutions. One disadvantage of viscoelastic surfactants with long alkyl chains is that they solubilize nonpolar liquids on contact therewith, as a result of which the worm-like micelles are converted to spherical aggregates and the viscoelasticity is lost. Moreover, these viscoelastic surfactants, in contact with other surfactants, generally form mixed micelles, as a result of which the viscoelasticity can likewise be lost. Structures with short alkyl chains, or structures which deviate from the usual principle of linear construction of the surfactants, generally form spherical micelles or merely short anisometric aggregates, and hence do not form viscoelastic surfactant solutions.

Prior application EP 10163371.7 discloses derivatives of tris(2-hydroxyphenyl)methanes which optionally have further-functionalized terminal polyalkoxy groups, and the polyalkoxy groups may also be branched. The alkoxy groups used are, for example, ethyleneoxy groups or $C_1$- to $C_6$-alkyleneoxy groups. The derivatives are suitable for the production of viscoelastic surfactant solutions.

Prior application EP 11185626.6 discloses the use of these derivatives of tris(2-hydroxy-phenyl)methanes for tertiary mineral oil production.

It was an object of the invention to find novel derivatives of tris(2-hydroxyphenyl)methanes, which should be suitable especially for formation of viscoelastic surfactant solutions.

Accordingly, derivatives of tris(2-hydroxyphenyl)methane have been found, where the tris(2-hydroxyphenyl)methane derivatives have the general formula (I)

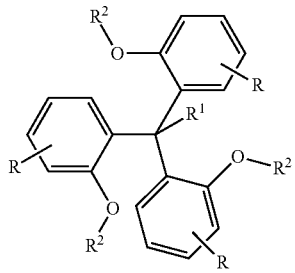

(I)

and the $R^1$, $R^2$ and R radicals are each defined as follows:

R: each independently 0 to 4 $C_1$- to $C_{30}$-hydrocarbyl radicals per phenyl ring, $R^1$: a radical selected from the group of H, OH, F, Cl, Br, I and $C_1$- to $C_{30}$-hydrocarbyl groups, $R^2$: each independently radicals of the general formula —($-R^5$—O—$)_n$—$R^6$—X (III), where $R^5$, $R^6$, X, m and n are each independently defined as follows:

n: a number from 1 to 50, $R^5$: each independently groups of the general formula —$CH_2$—$CH(R^7)$—(—$CH_2$)$_m$— (VI), where m is 0 or 1 and $R^7$ is a radical selected from the group of H, $C_1$- to $C_6$-hydrocarbyl groups and oxygen-containing functional groups, $R^6$: a single bond or an alkylene group which has 1 to 10 carbon atoms and may optionally have functional groups as substituents, X: H or a hydrophilic group, wherein the compound (I) comprises at least one $R^5$ radical of the general formula —$CH_2$—$CH(R^{7a})$— (IVa) where $R^{7a}$ is a group selected from the group of —$COOR^8$ and —$CH_2$—O—(—$CH_2$—$CH(R^9)$—O—$)_z$—$R^{10}$, and $R^8$, $R^9$, $R^{10}$ and z are each defined as follows:

$R^8$: H, an a-valent ion of the general formula 1/a $M^{a+}$, where a=1, 2 or 3 or a hydrocarbyl group having 1 to 6 carbon atoms, $R^9$: H or a hydrocarbyl group having 1 to 6 carbon atoms, $R^{10}$: H or a hydrocarbyl group having 1 to 6 carbon atoms, z: a number from 1 to 20.

Additionally found have been the preparation of such compounds and the use thereof, more particularly as surfactants, thickeners and for mineral oil production.

The following specific details of the invention are given:
Inventive Compounds

The inventive compounds are derivatives of tris(2-hydroxyphenyl)methane of the general formula (I).

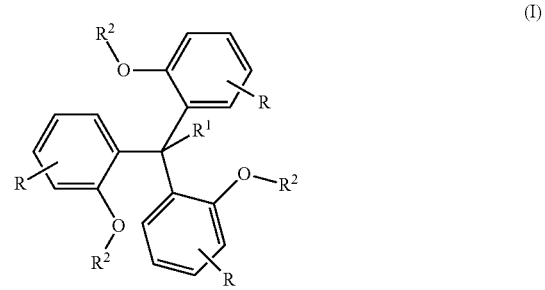

(I)

The $R^1$ radical is a radical selected from the group of H, OH, F, Cl, Br, I, and straight-chain, branched or cyclic, aliphatic and/or aromatic $C_1$- to $C_{30}$-hydrocarbyl groups. Preference is given to H, Cl, a straight-chain or branched $C_1$- to $C_{12}$-alkyl group or a benzyl group. $R^1$ is more preferably H.

The three phenyl rings may each independently be substituted in the 3, 4, 5 and 6 positions by hydrocarbyl radicals R having 1 to 30 carbon atoms, where the groups may be in any arrangement. Preference is given to 1 or 2 R groups per phenyl ring. The R groups may be straight-chain, branched or cyclic, aliphatic and/or aromatic hydrocarbyl radicals. Preference is given preferably to straight-chain, branched or cyclic aliphatic hydrocarbyl groups having 1 to 20 and more preferably 1 to 12 carbon atoms. Examples of suitable R groups comprise methyl, ethyl, n-propyl, isopropyl, n-butyl, i-propyl, t-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl, adamantyl or benzyl groups.

The inventive compounds preferably have the general formula (II).

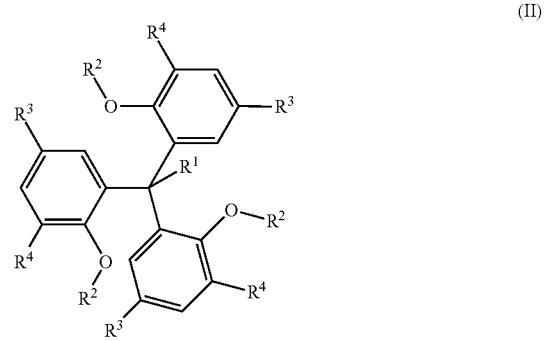

(II)

In formula (II), $R^3$ and $R^4$ are each independently H or hydrocarbyl radicals having 1 to 30 carbon atoms, preferably 1 to 20 carbon atoms and more preferably 1 to 12 carbon atoms. The hydrocarbyl radicals may be straight-chain, branched, cyclic, aliphatic and/or aromatic. They are preferably straight-chain, branched or cyclic aliphatic hydrocarbyl groups having 1 to 20 and more preferably 1 to 12 carbon atoms, and most preferably straight-chain or branched aliphatic hydrocarbyl radicals having 1 to 6 carbon atoms.

Examples of suitable hydrocarbyl groups comprise methyl, ethyl, propyl, isopropyl, n-butyl, i-butyl, t-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl or adamantyl groups.

$R^3$ and $R^4$ are preferably each H or methyl, ethyl, propyl, isopropyl, n-butyl, i-butyl, t-butyl, n-pentyl, 1,1-dimethylpropyl, 2,2-dimethylpropyl, 3-methylbutyl groups, 1,1,3,3-tetramethylbutyl, more preferably t-butyl groups.

In a preferred embodiment of the invention, at least one of the $R^3$ and $R^4$ radicals is not H; more preferably, the $R^3$ radical in this embodiment is not H. Most preferably, both $R^3$ and $R^4$ radicals are not H. Preferred, particularly preferred and very particularly preferred combinations of $R^3$ and $R^4$ radicals are specified in Tables 1, 2 and 3 below:

TABLE 1

List of preferred combinations

| $R^3$ | $R^4$ |
|---|---|
| t-Butyl | H |
| t-Butyl | Methyl |
| t-Butyl | Ethyl |
| t-Butyl | t-Butyl |
| Me | Me |
| Me | tBu |
| 1,1-Dimethylpropyl | H |
| 1,1-Dimethylpropyl | Methyl |
| 1,1-Dimethylpropyl | Ethyl |
| 1,1-Dimethylpropyl | t-Butyl |
| 1,1-Dimethylpropyl | 1,1-Dimethylpropyl |
| 1,1,3,3-Tetramethylbutyl | 1,1,3,3-Tetramethylbutyl |
| t-Butyl | 1,1,3,3-Tetramethylbutyl |

TABLE 2

List of particularly preferred combinations

| $R^3$ | $R^4$ |
|---|---|
| t-Butyl | Methyl |
| t-Butyl | t-Butyl |
| 1,1-Dimethylpropyl | Methyl |
| 1,1-Dimethylpropyl | 1,1-Dimethylpropyl |
| 1,1,3,3-Tetramethylbutyl | 1,1,3,3-Tetramethylbutyl |
| t-Butyl | 1,1,3,3-Tetramethylbutyl |

TABLE 3

List of very particularly preferred combinations

| $R^3$ | $R^4$ |
|---|---|
| t-Butyl | t-Butyl |
| 1,1-Dimethylpropyl | 1,1-Dimethylpropyl |
| 1,1,3,3-Tetramethylbutyl | 1,1,3,3-Tetramethylbutyl |
| t-Butyl | 1,1,3,3-Tetramethylbutyl |

Most preferably, both $R^3$ and $R^4$ are tert-butyl radicals.

The $R^2$ radicals in the abovementioned formulae (I) and (II) are each independently radicals of the general formula $-(R^5-O-)_n-R^6-X$ (III).

$R^5$ radicals in formula (III) are each independently groups of the general formula $-CH_2-CH(R^7)-(-CH_2)_m-$ (IV).

In the formula (IV), m is 0 or 1, preferably 0. The groups may thus be 1,2-ethylene groups or 1,3-propylene groups having $R^7$ substituents.

In groups where m=0, the $R^7$ radical may, instead of the $-CH_2-CH(R^7)-$ orientation shown in formula (IV), also be incorporated into the polyoxyalkylene chain in the inverse orientation $-CH(R^7)-CH_2-$. The formula (IV) is intended to comprise both orientations, and it is of course also possible for both orientations to be present in one chain.

The $R^7$ radicals are each independently a radical selected from the group of H, $C_1$- to $C_6$-hydrocarbyl groups and oxygen-containing functional groups.

The $C_1$- to $C_6$-hydrocarbyl groups may be straight-chain, branched, saturated, unsaturated or aromatic hydrocarbyl groups. They are preferably aliphatic hydrocarbyl groups. Examples of such groups comprise methyl, ethyl, n-propyl or phenyl radicals.

Examples of oxygen-containing functional groups comprise $-OH$, $-CH_2OH$, $-CH_2OR^{11}$, where $R^{11}$ is a hydrocarbyl radical, preferably having 1 to 6 carbon atoms, polyalkoxy groups which may comprise a terminal OH group, or a further-functionalized OH group. Such groups may have the general formula $-(R^5-O-)_n-R^6-X$ where $R^5$, $R^6$, X and n are each defined as outlined above and below.

In the above radicals, X is in each case H or a hydrophilic group. Preferably, a hydrophilic group comprises one or more oxygen atoms. According to the type of $R^2$ radical, it is possible for only one X group or else a plurality of X groups to be present in one $R^2$ radical. Hydrophilic groups may especially be acidic groups, preferably a group selected from the group of carboxyl groups $-COOM$, sulfo groups $-SO_3M$, sulfate groups $-OSO_3M$, phosphonic acid groups $-PO_2M_2$ or phosphoric acid groups $-OPO_3M_2$, where M is $H^+$ or a k-valent counterion $1/kY^{k+}$. The acidic groups may thus be present as the free acid and/or as a salt thereof. When M is not $H^+$, it is preferably a monovalent counterion, for example $NH_4^+$, ammonium ions with organic radicals or alkali metal ions. Preferred acidic groups are those selected from the group of carboxyl groups $-COOM$, sulfo groups $-SO_3M$ and sulfate groups $-OSO_3M$, more preferably sulfate groups $-OSO_3M$.

Preferred hydrophilic groups further comprise radicals which comprise at least one, preferably at least 2, OH groups, especially mono- or oligosaccharide radicals, preferably monosaccharide radicals. The saccharides may in principle be all kinds of saccharides. It is possible with preference to use radicals derived from pentoses and hexoses, especially from hexoses. Examples of suitable monosaccharides comprise glucose, mannose, galactose, fructose or ribose. It is possible with preference to use radicals derived from glucose. Derivatives of the saccharides may also be involved, for example products originating from the saccharides through reduction or oxidation. More particularly, such derivatives may be sugar acids, for example gluconic acid.

Examples of other hydrophilic groups comprise, for example, amine oxide groups.

$R^6$ is a single bond or an alkylene group having 1 to 10 carbon atoms, preferably 1 to 3 carbon atoms, which may optionally have functional groups as substituents, especially an OH group. Examples of such groups comprise $-CH_2-$, $-CH_2CH_2-$, $-CH_2-CH_2-CH_2-$ or $-CH_2-CH(OH)-CH_2-$ groups.

The number n is a number from 1 to 50, preferably 2 to 40 and more preferably 3 to 30 and, for example, 5 to 20.

As explained above, an $R^7$ radical may in turn comprise $-R^5-O-$ units, which means that the polyalkoxy groups $R^2$ need not necessarily be linear, but may also be branched. The total number of all $R^5$ groups in an $R^2$ radical, i.e. of $R^5$ groups in the main group and of $R^5$ groups in any branches present, will be referred to hereinafter as z. In the case that the group is a linear $R^2$ group, z corresponds to the number n. Preferably, z is a number from 3 to 50.

The numbers n and z are based in a known manner on the average of the alkoxy groups present in the molecule, and the average need not of course be a natural number, but may also be a positive rational number.

According to the invention, the compound (I) comprises at least one $R^5$ radical of the general formula —$CH_2$—CH($R^{7a}$)— (IVa) where $R^{7a}$ is a group selected from the group of —$COOR^8$ and —$CH_2$—O—(—$CH_2$—CH($R^9$)—O—$)_z$—$R^{10}$.

$R^8$ here is H, an a-valent ion of the general formula 1/a $M^{a+}$, where a=1, 2 or 3, or a $C_1$- to $C_6$-hydrocarbyl group.

The hydrocarbyl group is preferably an aliphatic hydrocarbyl group and more preferably a methyl or ethyl group. The M ions are preferably monovalent ions, especially alkali metal ions, for example $Li^+$, $Na^+$ or $K^+$ ions, or ammonium ions of the general formula $NR_4^{11}$ where the $R^{11}$ radicals are each independently H or a hydrocarbyl radical, for example a hydrocarbyl radical having 1 to 6 and preferably 1 or 2 carbon atoms. Examples of ammonium ions comprise $NH_4^+$, $N(CH_3)_4^+$ and $N(C_2H_5)_4^+$. In other words, the —$COOR^8$ group may be thus, in one embodiment of the invention, be a carboxyl group —COOH or salt thereof, and, in another embodiment, it may be an ester group, preferably a methyl ester or ethyl ester group. It is of course also possible for both kinds of —$COOR^8$ groups to be present in one $R^2$ radical.

$R^9$ and $R^{10}$ are each H or a hydrocarbyl group having 1 to 6 carbon atoms, where the hydrocarbyl groups are preferably methyl or ethyl groups. Z is a number from 1 to 20, preferably 2 to 10 and more preferably 2 to 5.

It is preferable that at least 50 mol % of the $R^9$ groups present in a radical are H, preferably at least 75%, and $R^9$ is most preferably exclusively H.

The $R^{10}$ group is preferably a methyl group.

The person skilled in the art makes an appropriate selection among the possible groups (III) and the $R^1$, $R^2$, $R^3$ and $R^4$ radicals according to the desired end use of the compounds.

In a preferred embodiment of the invention, the compounds (I), as well as the groups with the $R^{7a}$ radicals, also comprise —$CH_2$—CH($R^{7b}$)— (IVb) radicals where $R^{7b}$ is selected from the group of H, methyl and ethyl. In general, at least 50 mol % of the $R^{7b}$ groups present in a radical are H, preferably at least 75%, and $R^{7b}$ is most preferably exclusively H.

The alkoxy groups (IVa) with the $R^{7a}$ radicals and the alkoxy groups (IVb) with the $R^{7b}$ radicals may be arranged in any desired manner, for example randomly, in blocks, in an alternating manner or with a gradient. The arrangement is preferably a blockwise arrangement, with the groups (IVb) with the $R^{7a}$ radicals preferably arranged terminally.

In one embodiment of the invention, the $R^2$ radicals are each independently radicals of the general formula —(—$CH_2$—CH($R^{7b}$)—O—$)_a$—(—$CH_2$CH(—$COOR^8$)—O—$)_b$—H (V), where the alkylene oxide blocks are arranged in the sequence mentioned, $R^{7b}$ and $R^8$ are each as defined above and a and b are each integers from 1 to 49, where the sum of a+b is 1 to 50. Preferably, a is 2 to 30 and b is 1 to 20, with the proviso that a>b. More preferably, a is 5 to 20 and b is 1 to 10, with the proviso that a>b.

In addition, in the general formula (V), $R^8$ is preferably H or an ion 1/a $M^{a+}$ as defined above, preferably H, an alkali metal ion or an ammonium ion, especially $NH_4^+$. More preferably, the radicals (V) are —(—$CH_2$—$CH_2$—O—$)_a$—(—$CH_2$CH(—$COOR^8$)—O—$)_b$—H.

Preparation of the Inventive Compounds

To prepare the inventive compounds, it is first possible to synthesize tris(2-hydroxyphenyl)methane compounds of the general formula (VI) or (VII) with the desired substitution pattern with regard to $R^1$, and R and $R^3$ and $R^4$.

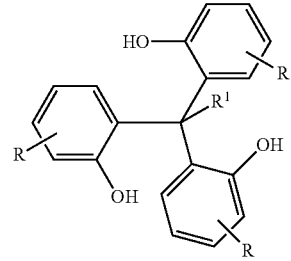

(VI)

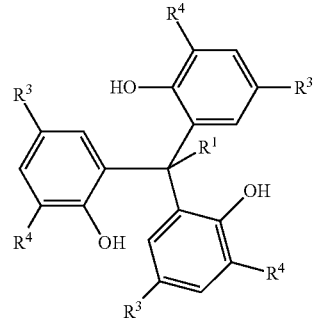

(VII)

The methods for preparation of the compounds are described in detail in the literature cited at the outset, for example G. Casiraghi, G. Casnati and M. Cornia, Tetrahedron Letters, No. 9, 679-682 (1973), M. B. Dinger and M. J. Scott, Chem. Commun., 1999, 2525/2526, Inorg. Chem. 2000, 39, 1238-1254 and Inorg. Chem. 2001, 40, 1029-1036, M. B. Dinger and M. J. Scott, Eur J. Org. Chem. 2000, 2467-2478, K. Matloka, A. Gelis, M. Regalbuto, G. Vandegift and M. J. Scott, Dalton Trans., 2005, 3719-3721, M. W. Peters, E. J. Werner and M. J. Scott, Inorg. Chem., 2002, 41, 1701-1716 and R. Mitra, M. W. Peters and M. Scott, Dalton Trans., 2007, 3924-3935.

The tris(2-hydroxyphenyl)methane compounds of the general formulae (VI) and (VII) can be alkoxylated in a manner known in principle in a second step. The performance of alkoxylations is known to those skilled in the art. It is likewise known to those skilled in the art that the molecular weight distribution of the alkoxylates can be influenced through the reaction conditions, more particularly the selection of the catalyst.

For alkoxylation, at least alkylene oxides of the general formulae

 and/or (VIIIa)

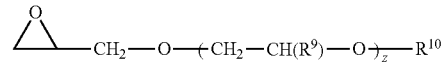 (VIIIb)

are used, where R[8] in the case of alkylene oxide (VIIIa) is a hydrocarbyl radical having 1 to 6 hydrocarbon atoms, i.e. esters are used. It is possible to obtain carboxylic acid groups or salts thereof from these by hydrolysis after the alkoxylation.

If other alkylene oxide units are to be present in the radicals as well as the alkylene oxides mentioned, further alkylene oxides are used as well as the alkylene oxides (VIIIa) and/or (VIIIb), for example $C_2$- to $C_8$-alkylene oxides such as ethylene oxide, propylene oxide, butylene oxide or styrene oxide.

In order to obtain —$CH_2$—$CH(R^7)$—$CH_2$— units, i.e. m=1, it is possible to use glycidol (IXa)

(IXa)

The alkoxylation gives rise to a chain with a —$CH_2$—$CH(OH)$—$CH_2OH$ end group, it being possible for further alkylene oxide units to add onto each of the OH groups in the course of continued alkoxylation, thus obtaining branched $R^2$ groups.

Units with side groups $R^7$=—$CH_2OH$ can be obtained using protected glycidol (IXb).

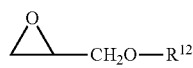
(IXb)

$R^{12}$ may in principle be all kinds of groups with which the OH function can be protected during the alkoxylation, for example t-butyl group or benzyl groups. The protecting groups can be detached in a manner known in principle after the alkoxylation and optionally after introduction of the —$R^6$—X groups, to give —$CH_2OH$ groups.

The alkoxylation may be a base-catalyzed alkoxylation. For this purpose, the tris(2-hydroxyphenyl)methane compounds can be admixed in a pressure reactor with alkali metal hydroxides, preferably potassium hydroxide, or with alkali metal alkoxides, for example sodium methoxide. By means of reduced pressure (for example <100 mbar) and/or an increase in the temperature (30 to 150° C.), water still present in the mixture can be drawn off. Thereafter, the alcohol is present as the corresponding alkoxide. Subsequently, inert gas (e.g. nitrogen) is used for inertization and the alkylene oxide(s) is/are added stepwise at temperatures of 60 to 180° C. up to a pressure of max. 10 bar. At the end of the reaction, the catalyst can be neutralized by addition of acid (e.g. acetic acid or phosphoric acid) and can be filtered off if required. Optionally, the alkoxylation can also be performed in the presence of a solvent. This may be, for example, toluene, xylene, dimethylformamide or ethylene carbonate.

The alkoxylation of the alcohols can, however, also be undertaken by means of other methods, for example by acid-catalyzed alkoxylation. It is also possible to use, for example, double hydroxide clays as described in DE 43 25 237 A1, or it is possible to use double metal cyanide catalysts (DMC catalysts). Suitable DMC catalysts are disclosed, for example, in DE 102 43 361 A1, especially paragraphs [0029] to [0041], and the literature cited therein. For example, it is possible to use catalysts of the Zn—Co type. To perform the reaction, the alcohol R—OH can be admixed with the catalyst, and the mixture can be dewatered as described above and reacted with the alkylene oxides as described. Typically not more than 1000 ppm of catalyst based on the mixture are used, and the catalyst can remain in the product due to this small amount. The amount of catalyst may generally be less than 1000 ppm, for example 250 ppm or less.

The alkoxylation can alternatively also be undertaken by reaction of the compounds (VI) and (VII) with cyclic carbonates, for example ethylene carbonate.

By means of the alkoxylation, inventive compounds are obtained directly, namely those where X=H. These have terminal OH groups. This is shown in FIGURE (X) below, by way of example with inventive compounds.

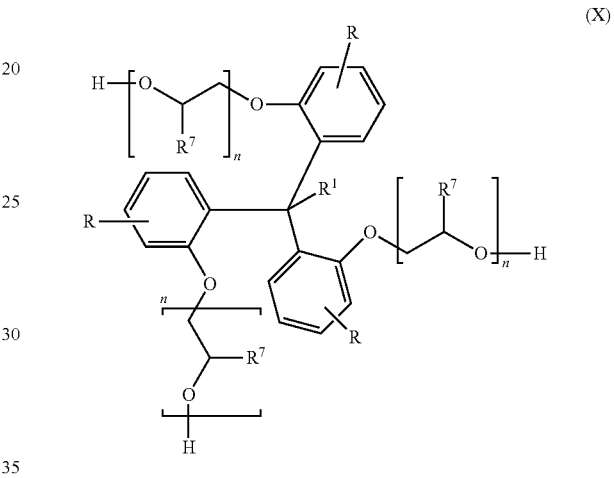
(X)

To introduce X groups which are not H, the alkoxylated tris(2-hydroxyphenyl)methane derivatives of the formula (X) having terminal OH groups are functionalized further with —$R^6$—X groups in a suitable manner. This gives compounds of the general formula (XI).

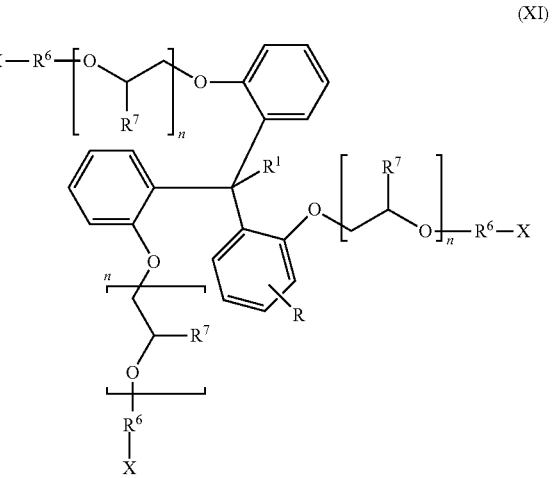
(XI)

Derivatives comprising sulfate groups —$OSO_3M$ can be obtained by reaction of the terminal OH groups with $SO_3$, sulfuric acid, chlorosulfuric acid or aminosulfonic acid (CAS No. 5329-14-6) and subsequent neutralization with, for example, sodium hydroxide solution. This can be performed, for example, in a falling-film reactor. This reaction substitutes only the terminal OH groups with sulfate groups. $R^6$ in this reaction is a single bond.

Derivatives comprising sulfonate groups —$SO_3M$ can be obtained by substitution of the OH group for Cl using phosgene or thionyl chloride. The conversion can be undertaken in the presence of a solvent, for example chlorobenzene. HCl released and $CO_2$ or $SO_2$ released can advantageously be removed from the system by stripping with nitrogen, such that ether cleavage is suppressed. The alkyl alkoxy chlorine compound is subsequently reacted with an aqueous solution of sodium sulfite, the chloride being substituted by sulfite to obtain the sulfonate. The substitution can be undertaken in the presence of a phase mediator (for example $C_1$- to $C_8$-alcohols) at a temperature of 100-180° C. under pressure. The sulfonates can alternatively be obtained by addition of vinylsulfonic acid onto the compound (V). Details thereof are described, for example, in EP 311 961 A1. Sulfonates can also be obtained by reacting the compounds (V) with 1,3-propane sultone or 1,4-butane sultone. This gives sulfonates with a terminal —$CH_2$—$CH_2$—$CH_2$—$SO_3M$ (i.e. $R^6$=—$CH_2$—$CH_2$—$CH_2$—) or —$CH_2$—$CH_2$—$CH_2$—$CH_2$—$SO_3M$ (i.e. $R^6$=—$CH_2$—$CH_2$—$CH_2$—$CH_2$—) group. Compounds with a terminal —$CH_2$—CH(OH)—$CH_2$—$SO_3M$ group (i.e. $R^6$=—$CH_2$—CH(OH)—$CH_2$—) can be obtained by reaction of the compound (V) with epichlorohydrin and subsequent nucleophilic substitution of the chloride group by sodium sulfite.

Derivatives comprising carboxylate groups —COOM can be obtained by oxidation of the compound (V). All oxidizing agents are suitable for this purpose, optionally in combination with suitable catalysts which can oxidize the terminal OH group of the compound (V) to the COOH group, without oxidizing other parts of the molecule to any great extent. The oxidation can be undertaken, for example, with the aid of air or oxygen using a noble metal catalyst (for example a catalyst based on palladium). This synthesis variant gives a terminal —$CH_2$—COOM group (i.e. $R^6$=—$CH_2$—). Carboxylates can additionally also be prepared by adding (meth)acrylic acid or a (meth)acrylic ester onto the OH groups by means of a Michael addition. If the esters are used, these are hydrolyzed after the addition. This synthesis variant—according to whether acrylic acid or (meth)acrylic acid or esters thereof have been used—gives terminal —$CH_2$—$CH_2$—COOM or —$CH_2$—CH($CH_3$)—COOM groups.

Phosphate groups can be introduced by reaction with phosphorus pentoxide, phosphonate groups by reaction with vinylphosphonic acid.

Compounds with mono- or oligosaccharide groups can be prepared by converting the appropriate saccharide, for example glucose, with the aid of an acidic catalyst, for example para-toluenesulfonic acid, and n-butanol to the corresponding butyl acetal. The water of reaction which forms can be removed from the reaction mixture by application of reduced pressure. Thereafter, the compound (V) is added and the transacetalization is driven by distillative removal of the butanol from the equilibrium. The acidic catalyst can be neutralized at the end of the reaction by addition of base, for example NaOH or KOH.

According to the type of $R^2$ groups, the compounds obtained have only one terminal —$R^6$—X group, or else several terminal and/or pendant —$R^6$—X groups.

In the case of introduction of the terminal —$R^6$—X group, it is of course not necessary to convert all OH groups of OH-terminated inventive compounds. It is possible to convert only a portion of the groups, for example only every third group on average. In this way, it is possible to adapt the properties of the inventive compounds to the desired end use.

In the case of glycidol, various synthesis variants are conceivable. If unprotected glycidol is used, the $R^2$ groups may be branched and have several terminal or lateral OH groups. These groups may be converted fully or else only partly to —$R^6$—X groups. In the case of only partial conversion, the conversion is random.

If protected glycidol is used, what is formed first of all is an unbranched polyalkoxy chain with a terminal OH group and pendant protected OH groups. The protecting groups can then first be removed and then the introduction of the —$R^6$—X groups can be undertaken. In this case, what is formed is a linear $R^2$ group which has terminal and/or pendant —$R^6$—X groups. If, in an alternative synthesis, the protecting groups are not eliminated at first, but the introduction of the —$R^6$—X groups is undertaken first, only the terminal OH groups react. The detachment of the protecting groups may follow. In this case, what is formed is an $R^2$ group which has a terminal —$R^6$—X group and additionally pendant methylol groups —$CH_2OH$.

Compounds (I) with —$COOR^8$ groups in which $R^8$ is H or an ion can be obtained by, as described, first preparing a compound —$COOR^8$ in which $R^8$ is a hydrocarbon group. This can be hydrolyzed in a further process step in a manner known in principle.

Use of the Inventive Compounds

The novel compounds are suitable for use as surfactants. They are therefore especially suitable for production of viscoelastic surfactant solutions and can therefore be used as a component of thickening formulations.

Due to their interface-active properties, but also due to their thickening action, the novel compounds are also suitable, for example, for use in washing and cleaning compositions, dyes and paints, cosmetic and pharmaceutical formulations, paper, textile and leather assistants, formulations for human and animal nutrition, the construction sector, crop protection formulations, and generally for production of emulsions and dispersions.

In a preferred embodiment of the invention, the inventive compounds can be used in processes for mineral oil production, more particularly for tertiary mineral oil production.

In the case of the inventive use for mineral oil production, at least one production well and at least one injection well are sunk into a mineral oil deposit. In general, a deposit is provided with several injection wells and with several production wells.

Through the at least one injection well, an aqueous formulation of the tris(2-hydroxyphenyl)methane derivatives (I) described is injected into the mineral oil deposit, and mineral oil is withdrawn from the deposit through at least one production well. The term "mineral oil" in this context does not mean only single-phase oil; instead, the term also comprises the customary crude oil-water emulsions. By virtue of the pressure generated by the formulation injected, the mineral oil flows in the direction of the production well and is produced via the production well.

The deposit temperature of the mineral oil deposit to which the process according to the invention is applied is, in accordance with the invention, 10 to 150° C., preferably 10° C. to 120° C. and, for example, 20° C. to 70° C.

The person skilled in the art is aware that a mineral oil deposit often has a homogeneous temperature based on time and area, except in the case of thermal measures. The deposit temperature mentioned is based on the region of the deposit between the injection and production wells, which is covered by the injected composition. Methods for determination of the temperature of a mineral oil deposit are known in principle to those skilled in the art. The temperature is generally undertaken from temperature measurements at particular sites in the formation.

The process can be employed especially in the case of mineral oil deposits with an average permeability of 100 mD to 154 D, preferably 150 mD to 2 D and more preferably 200 mD to 1 D. The permeability of a mineral oil formation is reported by the person skilled in the art in the unit of "darcies" (abbreviated to "D" or "mD" for "millidarcies"), and can be determined from the flow rate of a liquid phase in the mineral oil formation as a function of the pressure differential applied. The flow rate can be determined in core flooding tests with drill cores taken from the formation. Details thereof can be found, for example, in K. Weggen, G. Pusch, H. Rischmüller in "Oil and Gas", pages 37 ff., Ullmann's Encyclopedia of Industrial Chemistry, Online edition, Wiley-VCH, Weinheim 2010. It is clear to the person skilled in the art that the permeability in a mineral oil deposit need not be homogeneous, but generally has a certain distribution, and the specification of the permeability of a mineral oil deposit is accordingly an average permeability.

For the inventive use, an aqueous formulation comprising, as well as water, at least one of the tris(2-hydroxyphenyl)methane derivatives (I) described is used. It is also possible to use mixtures of different tris(2-hydroxyphenyl)methane derivatives. The formulation can be made up in freshwater, or else in water containing salts. Mixtures of different salts may be involved.

For example, it is possible to use seawater to make up the aqueous formulation, or it is possible to use produced formation water which is reused in this manner. In the case of offshore production platforms, the formulation is generally made up in seawater. In the case of onshore production facilities, the tris(2-hydroxyphenyl)methane derivative can advantageously first be dissolved in freshwater, and the resulting solution can be diluted to the desired use concentration with formation water. The formulation can preferably be produced by initially charging the water, scattering in the tris(2-hydroxyphenyl)methane derivative as a powder and mixing it with the water.

The salts may especially be alkali metal salts and alkaline earth metal salts. Examples of typical cations comprise $Na^+$, $K^+$, $Mg^{2+}$ or $Ca^{2+}$ and $Mg^{2+}$. Examples of typical anions comprise chloride, bromide, hydrogencarbonate, sulfate or borate.

When the formulation comprises salts, generally at least one or more than one alkali metal ion is present, especially at least $Na^+$. In addition, it is also possible for alkaline earth metal ions to be present, in which case the weight ratio of alkali metal ions/alkaline earth metal ions is generally $\geq 2$, preferably $\geq 3$. The anions present are generally at least one or more than one halide ion, especially at least $Cl^-$. In general, the amount of $Cl^-$ is at least 50% by weight, preferably at least 80% by weight, based on the sum of all anions.

The total amount of all salts in the aqueous formulation is frequently 10 000 ppm to 350 000 ppm (parts by weight), based on the sum of all components of the formulation.

When seawater is used to make up the formulation, the salt content is generally 20 000 ppm to 50 000 ppm and, when formation water is used, generally 100 000 ppm to 250 000 ppm. The amount of alkaline earth metal ions may preferably be 1000 to 53 000 ppm. The aqueous formulation may also comprise further components, for example biocides, stabilizers and inhibitors.

The concentration of the tris(2-hydroxyphenyl)methane derivative is fixed such that the aqueous formulation has the desired viscosity for the end use. The viscosity of the formulation should generally be at least 3 mPas (measured at 25° C. and a shear rate of, for example, 7 $s^{-1}$, or as preferentially occurs in the reservoir), preferably at least 10 mPas.

According to the invention, the concentration of the tris(2-hydroxyphenyl)methane derivatives in the formulation is 0.01 to 10% by weight, often 0.05 to 10% by weight, based on the sum of all components of the aqueous formulation. Preferably, the amount is 0.05 to 5% by weight, more preferably 0.05 to 1% by weight and, for example, approx. 0.1% by weight.

The injection of the aqueous formulation can be undertaken by means of customary apparatus. The formulation can be injected into one or more injection wells by means of customary pumps. The injection wells are often lined with steel tubes cemented in place in the region of the mineral oil deposit, and the steel tubes are perforated at the desired point. The formulation enters the mineral oil formation from the injection well through the perforation. In a manner known in principle, the pressure applied by means of the pumps fixes the flow rate of the formulation and hence also the shear stress with which the aqueous formulation enters the formation. The shear stress on entry into the formation can be calculated by the person skilled in the art in a manner known in principle on the basis of the Hagen-Poiseuille law using the flow area on entry into the formation, the mean pore radius and the volume flow rate. The average permeability or porosity of the formation can be determined in a manner known in principle by measurements on drill cores. Of course, the greater the volume flow rate of aqueous formulation injected into the formation, the greater the shear stress.

The rate of injection can be fixed by the person skilled in the art according to the properties of the formation (permeability, thickness) and the requirements of the mineral oil field (number of injectors, configuration thereof, etc.).

Preferably, the shear rate on entry of the aqueous formulation into the formation is at least 30 000 $s^{-1}$, preferably at least 60 000 $s^{-1}$ and more preferably at least 90 000 $s^{-1}$.

Frequently used concentrations and further components of the aqueous formulation:
  A) Concentrations are often in the range of 0.01-10% by weight, often 0.05-10% by weight, preferred concentrations are between 0.1-1% by weight and particularly preferred concentrations between 0.1 and 0.5% by weight, based in each case on the overall formulation.
  B) Solvents can be used as further component. Typically, the derivative of tris(2-hydroxyphenyl)methane is dissolved in the formation water. Dissolution in seawater is also possible. Predissolution with a water-miscible solvent, e.g. ethanol or isopropanol, to prepare concentrates with higher active content is possible. It is also possible to use spring water.
  C) Salts influence the viscosity of the formulations. The target viscosity is often established under deposit salinity via variation of the concentration.
  D) Dependence of the pH of the formulation on the thickening properties or the viscosity (for example in the case of use of carboxylates) is possible.
  E) A combination of the derivative of tris(2-hydroxyphenyl)methane with one or more further surfactants is possible.

F) It is optionally also possible to use further components, such as biocides, in the formulation. In general, biocides are already used for water flooding. Especially waters of low salinity can be treated with algicides, fungicides, etc.

The examples which follow are intended to illustrate the invention in detail.

Preparation of the Starting Compound

Synthesis of
tris(3,5-di-tert-butyl-2-hydroxyphenyl)methane

Tris(3,5-di-tert-butyl-2-hydroxyphenyl)methane (CAS No. 143560-44-5) was prepared by means of the process described by M. B. Dinger, M. J. Scott, *Eur. J. Org. Chem.* 2000, 2467. Tris(3,5-di-tert-butyl-2-hydroxyphenyl)methane is also abbreviated to TRIS hereinafter.

EXAMPLE 1

Synthesis of TRIS[(—CH$_2$—CH$_2$—O)$_9$H]$_3$ by Ethoxylation of TRIS with 27 EO Units

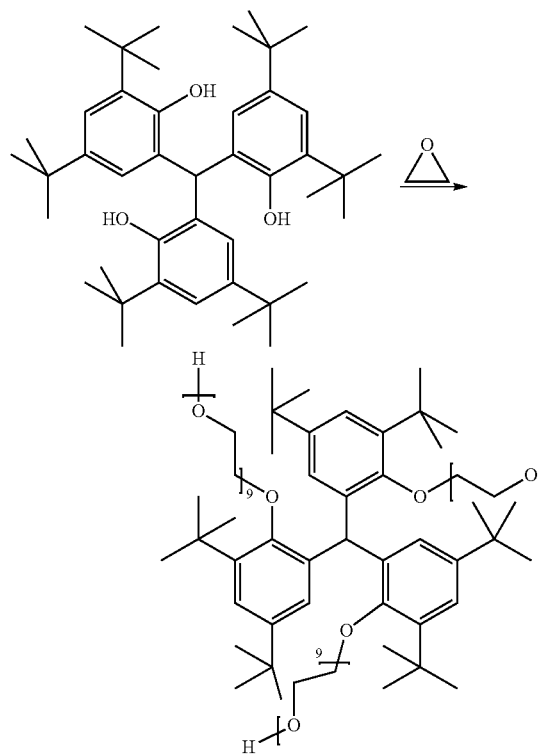

In a 2 l pressure reactor, 50 g of TRIS are dissolved in toluene together with 3.3 g of crown ether (18-crown-6), and 1.4 g of potassium t-butoxide are added. The experimental mixture is purged thoroughly with nitrogen, a nitrogen supply pressure of 1.5 bar is established and the mixture is heated to 130° C. Subsequently, 25 g of ethylene oxide are added within 15 minutes, then 70 g of ethylene oxide within 90 minutes, in the course of which a distinctly exothermic reaction sets in. After metered addition has ended, the mixture is stirred at 130° C. for 5 hours, then at 50° C. for 12 hours. Thereafter, the mixture is purged with nitrogen and discharged from the reactor. 6.6 g of Ambersol® are added to the reaction solution which is degassed at 80° C. and 500 mbar for 2 hours. Subsequently, the solution is filtered through a Seitz Supradur® 200 depth filter, the solvent is distilled off from the filtrate and the product is dried at 80° C. and 2 mbar for 2 h. This gives 144 g of product (corresponds to 99.3% of theory). According to 1H NMR, the product corresponds to the desired structure.

EXAMPLE 2

Synthesis of TRIS[(—CH$_2$—CH$_2$—O—)$_9$—(—CH$_2$—CH(COOCH$_3$)—O—)$_2$—H]$_3$

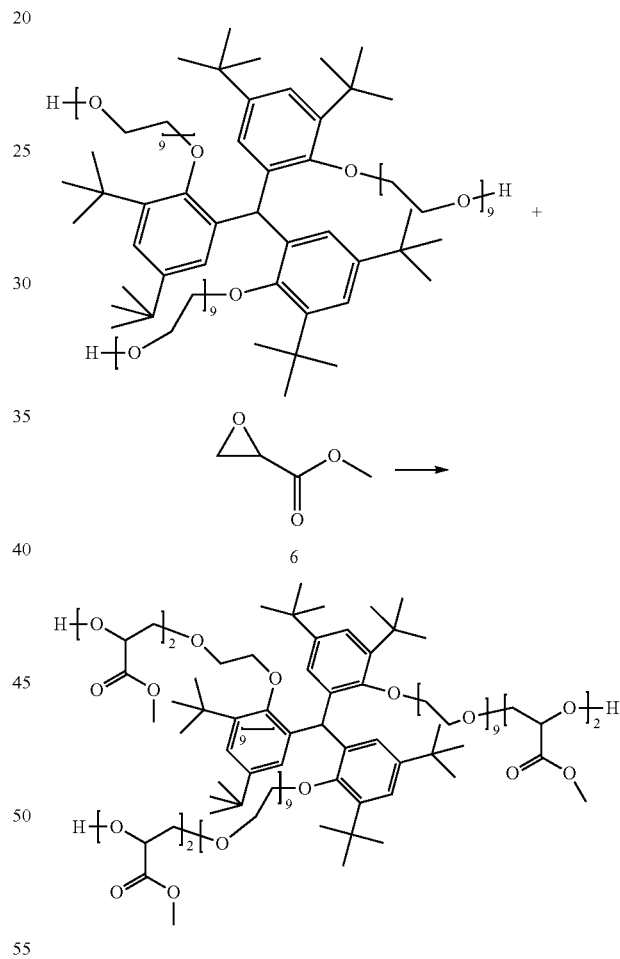

50 g of TRIS-27 EO, obtainable according to example 2, are heated to 100° C. together with 0.1 g of boron trifluoride etherate, and then 16.7 g of epoxypropionic acid methyl ester (EPSMe) are added dropwise. The reaction proceeds strongly exothermically and the mixture is kept between 100 and 150° C. by cooling in an ice bath. After complete addition, the mixture is stirred at 100° C. for a further 5 h. According to the gas chromatogram, no free epoxypropionic acid methyl ester (EPSMe) is present any longer. Yield: 65 g (corresponds to 98% of theory).

EXAMPLE 3

Synthesis of TRIS[(—CH$_2$—CH$_2$—O—)$_9$—(—CH$_2$—CH(COONa)—O—)$_2$—H]$_3$

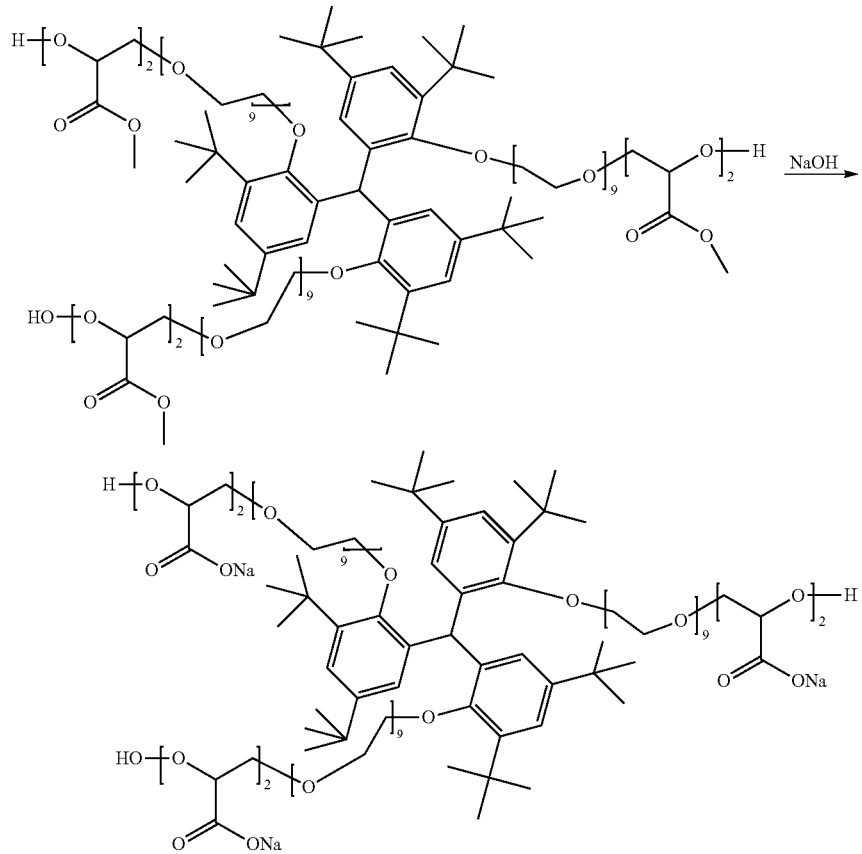

64 g of TRIS[(—CH$_2$—CH$_2$—O)$_9$—(—CH$_2$—CH(COOCH$_3$)—O—)$_2$—H]$_3$, obtainable according to example 2, are heated to 70° C., and 12.65 g of 50% sodium hydroxide solution are added dropwise within 15 minutes. The reaction proceeds exothermically and the reaction solution heats up to 80° C. After addition has ended, the mixture is stirred at 70° C. for a further 4 h. This is followed by successive addition of 40 g of water, 1 g of 50% sodium hydroxide solution and again 30 g of water. The pH of the solution toward the end of the reaction is 12. This gives 140 g of a red-brown, approx. 50% emulsion. The IR spectrum demonstrates complete hydrolysis.

The invention claimed is:

1. A derivative of tris(2-hydroxyphenyl)methanes, wherein the derivative is a compound of the general formula (I)

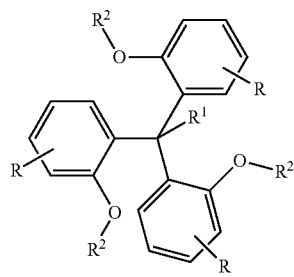

(I)

where the $R^1$, $R^2$ and R radicals are each defined as follows:

R: each independently 0 to 4 $C_1$- to $C_{30}$-hydrocarbyl radicals per phenyl ring, $R^1$: a radical selected from the group of H, OH, F, Cl, Br, I and $C_1$- to $C_{30}$-hydrocarbyl groups, $R^2$: each independently radicals of the general formula -(—$R^5$—O—)$_n$—$R^6$—X     (III),

where $R^5$, $R^6$, X, m and n are each independently defined as follows:

n: a number from 1 to 50, $R^5$: each independently groups of the general formula —CH$_2$—CH($R^7$)—(—H$_2$)$_m$—     (VI),

where m is 0 or 1 and $R^7$ is a radical selected from the group consisting of H, $C_1$- to $C_6$-hydrocarbyl groups, and oxygen-containing functional groups selected from the group consisting of —OH, —CH$_2$OH, —CH$_2$OR$^{11}$, and polyalkoxy groups optionally comprising a terminal OH group, wherein $R^{11}$ is a hydrocarbyl radical, $R^6$: a single bond or an alkylene group which has 1 to 10 carbon atoms and may optionally have functional groups as substituents, X: H or a hydrophilic group, wherein the compound (I) comprises at least one $R^5$ radical of the general formula —CH$_2$—CH($R^{7a}$)—     (IVa)

where $R^{7a}$ is a group selected from the group of —COOR$^8$ and —CH$_2$—O—(—CH$_2$—CH(R$^9$)—O—)$_z$—R$^{10}$, and R$^8$, R$^9$, R$^{10}$ and z are each defined as follows:

R$^8$: H, an a-valent ion of the general formula 1/a M$^{a+}$, where a=1, 2 or 3 or a hydrocarbyl group having 1 to 6 carbon atoms, R$^9$: H or a hydrocarbyl group having 1 to 6 carbon atoms, R$^{10}$: H or a hydrocarbyl group having 1 to 6 carbon atoms, and z: a number from 1 to 20.

2. The compound according to claim 1, wherein $R^{7a}$ is a —COOR$^8$ group and R$^8$ is a methyl and/or ethyl group.

3. The compound according to claim 1, wherein $R^{7a}$ is a —COOR$^8$ group and R$^8$ is H, an alkali metal ion or an ammonium ion.

4. The compound according to claim 1, wherein $R^{7a}$ is a —CH$_2$—O—(—CH$_2$—CH(R$^9$)—O—)$_z$—R$^{10}$ group where at least 50 mol % of the R$^9$ radicals present are H, and R$^{10}$ is a methyl or ethyl group and z is a number from 2 to 10.

5. The compound according to claim 1, wherein compounds (I), as well as (IVa) radicals, further comprise —CH$_2$—CH(R$^{7b}$)— (IVb) radicals where R$^{7b}$ is H, methyl and ethyl.

6. The compound according to claim 5, wherein $R^{7b}$ is H.

7. The compound according to claim 1, wherein the R$^2$ radicals are each independently radicals of the general formula

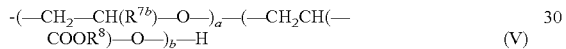

-(—CH$_2$—CH(R$^{7b}$)—O—)$_a$—(—CH$_2$CH(—COOR$^8$)—O—)$_b$—H    (V)

where the alkylene oxide blocks are arranged in the sequence specified, $R^{7b}$ and R$^8$ are each as defined in claim 1 and a and b are each numbers from 1 to 49, where the sum of a+b is 2 to 50.

8. The compound according to claim 7, wherein a is 2 to 30 and b is 1 to 20 in the formula (V), with the proviso that a>b.

9. The compound according to claim 7, wherein R$^8$ is H, an alkali metal ion or an ammonium ion.

10. The compound according to claim 1, wherein X is an acidic group selected from the group consisting of carboxyl groups —COOM, sulfo groups —SO$_3$M, sulfate groups —OSO$_3$M, phosphonic acid groups —PO$_2$M$_2$ and phosphoric acid groups —OPO$_3$M$_2$, where M is H$^+$ or a k-valent counterion 1/kY$^{k+}$.

11. The compound according to claim 1, wherein X comprises mono- or oligosaccharide radicals.

12. The compound according to claim 1, wherein the compounds have the general formula (II)

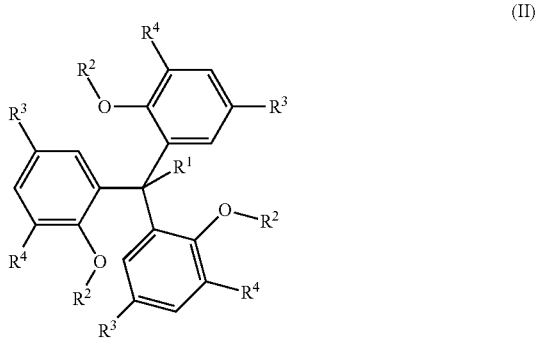

where R$^1$ and R$^2$ are each as defined above and R$^3$ and R$^4$ are each independently H or a C$_1$- to C$_{30}$-hydrocarbyl radical.

13. The compound according to claim 12, wherein R$^3$ and R$^4$ are each independently straight-chain or branched aliphatic C$_1$- to C$_6$-hydrocarbyl radicals.

14. The compound according to claim 13, wherein R$^3$ and R$^4$ are each t-butyl radicals.

15. A process for preparing the compound according to claim 1, which comprises providing a starting compound of the general formula (VI)

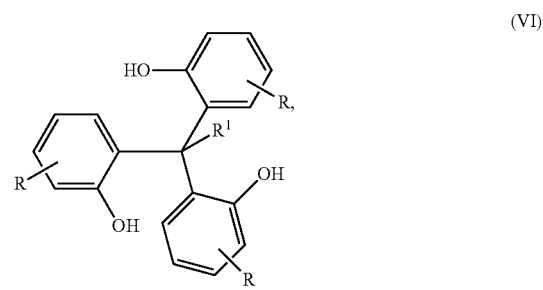

alkoxylating the material with alkylene oxides of the general formulae

where R$^8$ is a hydrocarbyl group having 1 to 6 carbon atoms, and/or

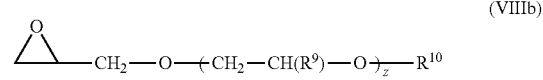

and optionally different C$_2$- to C$_8$-alkylene oxides, glycidol and cyclic C$_3$- to C$_9$-carbonates, and optionally substituting at least one terminal hydrogen atoms thereon for —R$^6$—X radicals.

16. The process according to claim 15, wherein alkylene oxides of the formula (VIIIa) are used and COOR$^8$ groups present, after the alkoxylation, the COOR$^8$ are hydrolyzed in a further process step to give —COOH groups or salts thereof.

17. A surfactant or thickener comprising the compound according to claim 1.

18. A process for production of washing and cleaning compositions, dyes and paints, cosmetic and pharmaceutical formulations, paper, textile and leather assistants, formulations for human and animal nutrition, the construction sector, crop protection formulations, and generally for production of emulsions and dispersions which comprises utilizing the compound according to claim 1.

19. A process for mineral oil production which comprises utilizing the compound according to claim 1.

20. The process according to claim 19, in which an aqueous formulation comprising at least one derivative of tris(2-hydroxyphenyl)methane of the general formula (I) is injected into a mineral oil deposit through at least one injection well and the crude oil is withdrawn from the deposit through at least one production well.

21. The process according to claim 20, wherein the temperature of the mineral oil deposit is 10 to 150° C.

22. The process according to claim 19, wherein the aqueous formulation comprises, as a further component, at least one salt in an amount of 10 000 ppm to 350 000 ppm.

23. The process according to claim 19, wherein the mineral oil production is effected from deposits with a deposit temperature of 10 to 150° C., said deposit comprising, as well as mineral oil, deposit water with a salinity of 20 000 ppm to 350 000 ppm, and the mineral oil having a viscosity (measured at deposit temperature) of at least 3 mPa*s, by injecting an aqueous formulation comprising at least one derivative of tris(2-hydroxyphenyl)methane of the formula (I) into the mineral oil deposit through at least one injection well and withdrawing crude oil from the deposit through at least one production well, said process comprising at least the following process steps:

providing at least one tris(2-hydroxyphenyl)methane derivative of the general formula (I) as a pure substance, mixture or concentrate;

preparing the aqueous formulation of the tris(2-hydroxyphenyl)methane component(s) by diluting the concentrate (K) provided in step (1) on site with water to a concentration of 0.01 g/l to 10 g/l, injecting the aqueous formulation of the tris(2-hydroxyphenyl)methane component(s) into the mineral oil formation, and withdrawing crude oil through at least one production well.

24. The process according to claim 19, wherein the derivative of tris(2-hydroxyphenyl)methane used is a derivative with unbranched $R^2$ radicals and the concentration of the tris(2-hydroxyphenyl)methane derivative in the formulation is 0.01 g/l to 5 g/l.

* * * * *